(12) United States Patent
Kodaka

(10) Patent No.: US 7,297,512 B2
(45) Date of Patent: Nov. 20, 2007

(54) METHOD FOR PRODUCING AMINO ACID COMPONENTS BY ENZYMATIC HYDROLYSIS OF FISH EGG SKIN

(75) Inventor: Kunihiko Kodaka, Fukuoka (JP)

(73) Assignee: Fuji Bio Technology Institute Co., Ltd., Fukuoka (JP)

(*) Notice: Subject to any disclaimer, the term of this patent is extended or adjusted under 35 U.S.C. 154(b) by 383 days.

(21) Appl. No.: 10/733,627

(22) Filed: Dec. 12, 2003

(65) Prior Publication Data

US 2004/0248239 A1  Dec. 9, 2004

(30) Foreign Application Priority Data

Jun. 9, 2003  (JP) ............................. 2003-163724

(51) Int. Cl.
  C12P 21/06  (2006.01)
  C12P 13/04  (2006.01)
  C12N 9/52  (2006.01)
  C12N 9/62  (2006.01)
  A61K 35/60  (2006.01)

(52) U.S. Cl. .................... 435/68.1; 435/106; 435/221; 435/225; 424/523

(58) Field of Classification Search ............... 435/68.1, 435/106, 220, 221, 222, 225; 424/523
See application file for complete search history.

(56) References Cited

U.S. PATENT DOCUMENTS 4,584,197 A * 4/1986 Takasaki et al. ............. 424/520
6,465,209 B1 * 10/2002 Blinkovsky et al. ....... 435/68.1

FOREIGN PATENT DOCUMENTS

| JP | 1-14885 | 3/1989 |
| JP | 03015368 A * | 1/1991 |
| JP | 5-93000 | 4/1993 |
| JP | 10-57016 | 3/1998 |
| JP | 10-276680 | 10/1998 |
| JP | 2000-50811 | 2/2000 |
| JP | 2003-180290 | 7/2003 |

OTHER PUBLICATIONS

JP 03015368 English language abstract obtained from Derwent on May 30, 2006 from WEST.*
Haraguchi et al. "Preserving effect of ozone on fish" Nippon Suisan Gakkaishi (1969) 35(9): 915-919, abstract only obtained from CAPLUS on STN, May 25, 2006.*
E. Seki et al., "Separation and Purification of Angiotensin I Converting Enzyme Inhibitory Peptides from Heated Sardine Meat by Treatment with Akaline Protease", Nippon Shokuhin Kogyo Gakkaishi, vol. 40, No. 11, pp. 783-791, 1993.

* cited by examiner

Primary Examiner—Leon B. Lankford, Jr.
Assistant Examiner—Susan Hanley
(74) Attorney, Agent, or Firm—Wenderoth, Lind & Ponack, L.L.P.

(57) ABSTRACT

From fish egg skin produced by utilization of roe grains of various fish, constituent proteins thereof are enzymatically degraded to obtain peptides and amino acids, of which effective utilization is achieved. The invention provides a method for producing amino acids and peptides (useful as nutrient enhancers for foods) from fish egg skins which comprises treating cold water-washed fish egg skins with ozonized water at room temperature or below, subsequently, degrading the resultant product with a proteolytic enzyme produced by *Bacillus subtilis*, or further treating with a proteolytic enzyme produced by *Aspergillus oryzae*, to degrade myogenic fiber proteins (contractile proteins: myosins) in the fish egg skin, and then concentrating/drying the degraded solution.

2 Claims, 1 Drawing Sheet

METHOD FOR PRODUCING AMINO ACID COMPONENTS BY ENZYMATIC HYDROLYSIS OF FISH EGG SKIN

BACKGROUND OF THE INVENTION

1. Field of the Invention

The present invention relates to a method for producing amino acid components from fish egg skin which is the skin of the hard roe of cod, herring, salmon, bonito and the like, said amino acid components being useful as physiologically active substances or nutrient enhancers.

2. Description of Related Art

Although fish wastes, such as fish meat, fish skin and fish bone, produced in conjunction with marine product processing are attempted to be utilized after being manufactured into fish powders, fish oils, feeds for the animal industry and fertilizers for agriculture, most of the fish egg skins produced during the processing of fish eggs and the marine processing are discarded as industrial wastes.

Moreover, for a method for utilizing fish and shellfish, the fish and shellfish are treated at high temperatures to inactivate autolytic enzymes contained in the fish and shellfish, and then constituent proteins are degraded with *Bacillus subtilis* proteases and *Aspergillus oryzae* proteases into peptide amino acids and free amino acids, whereby fish and shellfish extracts are obtained which are said to have pharmaceutical actions such as anti-ulcer action, insulin-like action and anti-hyperlipemia (cf. e.g., Patent Document 1).

Also, for methods for utilizing fish skins, fish bones and fish scales, considered is the method for treating the fish skins and the fish bones with proteases to give gelatin which will be utilized as a food material (e.g., see Patent Document 2), or the methods for utilizing, as a biomaterial for the medical use or a cosmetic material, collagen extracted from the fish scales (cf. e.g., Patent Document 3) and the fish skins (cf. e.g., Patent Document 4).

On the other hand, recent dry foods with a chili pepper taste for a side dish or as hors d'oeuvres for alcoholic beverages have been proposed, said dry foods which are produced by drying roe membranes of spiced walleye pollack eggs ("Mentaiko"; cf. e.g., Patent Document 5), but their commercial value as dry foods is questionable due to characteristics of the roe membrane of which the majority is made up of fiber protein.

Also, the present inventor has proposed a food seasoning with a Mentaiko flavor via enzymatically degrading Mentaiko-dipping sauces for the purpose of effectively utilizing the dipping sauces which are mass-produced (cf. e.g., Patent Document 6). This seasoning contains not only low molecular peptides and amino acid components produced from the degradation of proteins in the Mentaiko eggs and the skins thereof left in the dipping sauces, but also various mainly natural seasonings added for flavoring, and thus it would be expected as seasoning with Mentaiko taste.

However, concerning the utilization of fish egg skin per se produced in company with the utilization of various fish eggs, effective utilization thereof has not been proposed although most skins are made up of contractile proteins (myosins) which are myogenic fiber proteins (see Table 1: Ingredients of purified fish egg skin).

TABLE 1

| Ingredient | Edible part, per 100 g |
|---|---|
| Water | 7.0 g |
| Protein | 71.4 g |
| Lipid | Less than 0.1 g |
| Ash | 6.0 g |
| Sugar | 15.6 g |
| Dietary fiber | Less than 0.5 g |

[Patent Document 1]
JP-B-1-14885
[Patent Document 2]
JP-A-10-276680
[Patent Document 3]
JP-A-5-93000
[Patent Document 4]
JP-A-2000-50811
[Patent Document 5]
JP-A-10-57016
[Patent Document 6]
JP-2001-390691
[Non-Patent Document 1]
Food Science and Technology Research (Japan), Vol. 40, No. 11

SUMMARY OF THE INVENTION

It is an object of the present invention to provide environmental and dietary techniques for effectively utilizing waste products, fish egg skins, said technique which comprises enzymatically hydrolyzing myogenic fiber proteins (contractile proteins: myosins) which are component proteins for fish egg skins which are the roe skin of cod, herring, salmon and the like, and obtaining peptides and amino acids useful as physiologically active substances or nutrient enhancers for foods.

As a result of a study on the effective utilization of fish egg skins to accomplish the above object, the present inventor has succeeded in extracting the amino acids useful as physiologically active substances or nutrient enhancers for foods via pretreating the fish egg skin with ozonized water and then enzymatically hydrolyzing the myogenic fiber protein which is a component protein thereof.

The present invention provides:

1) a method for producing amino acids and peptides via the enzymatic hydrolysis of fish egg skins which comprises treating ozonized water-treated fish egg skins with a proteolytic enzyme produced by a microorganism of the *Bacillus* genus (including *Bacillus subtilis*) to degrade myogenic fiber proteins (contractile proteins) which constitute the fish egg skin, and collecting the resultant amino acid components; and 2) a method for producing amino acids and peptides via the enzymatic hydrolysis of fish egg skins which comprises treating ozonized water-treated fish egg skins with a proteolytic enzyme produced by a microorganism of the *Bacillus* genus (including *Bacillus subtilis*) and a proteolytic enzyme produced by a microorganism of the *Aspergillus* genus (including *Aspergillus oryzae*) to degrade myogenic fiber proteins (contractile proteins) which constitute the fish egg skin, and collecting the resultant amino acid components.

DETAILED DESCRIPTION OF PREFERRED EMBODIMENT(S)

Figure 1:
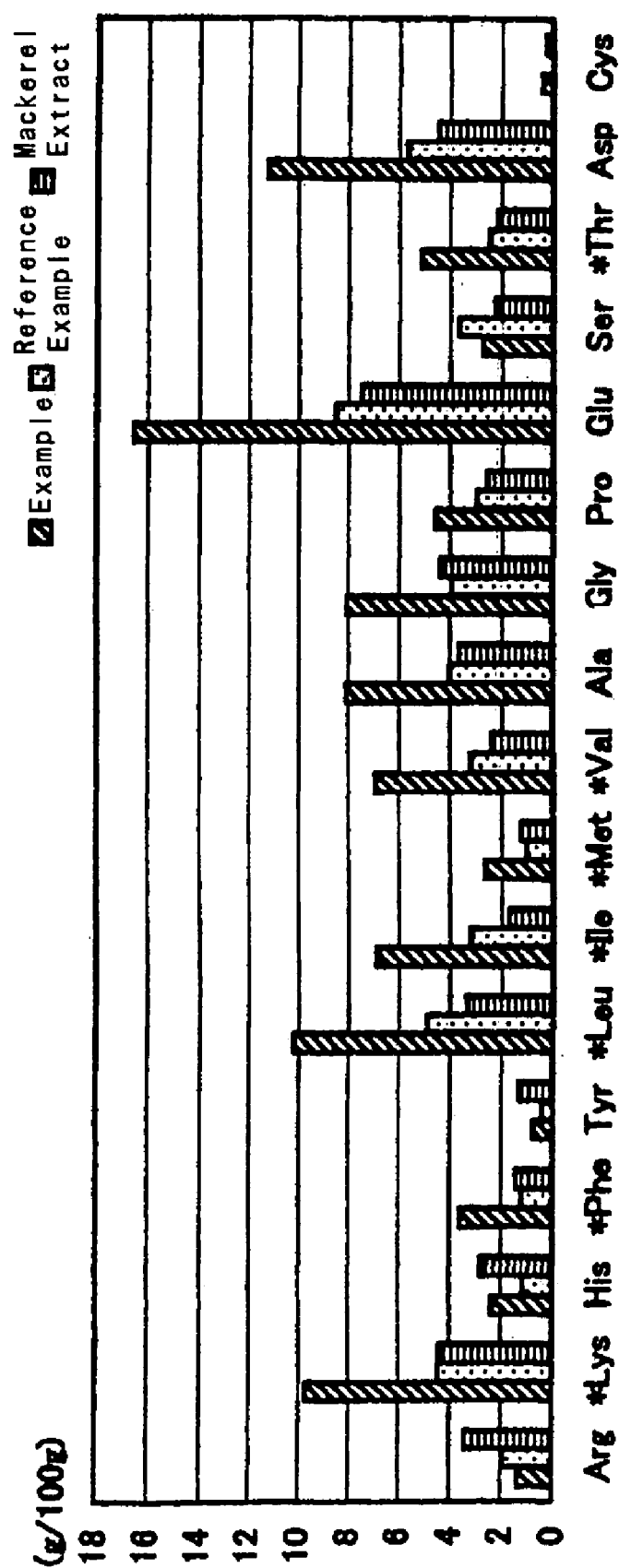
FIG. 1 is a graph of amino acid compositions for Example 1, reference example and mackerel extract.

In the method for producing amino acids and peptides (also referred to herein collectively as "amino acid components" or an "amino acid component") via the enzymatic hydrolysis of fish egg skins according to the invention, it is important to treat the fish egg skin with ozonized water at room temperature or below after washing the fish egg skin with cold water. The treatment with ozonized water at a low temperature leads to elimination of adherent bacteria and degreasing, and further, prevents the denaturation of the myogenic fiber protein, contractile protein (myosin) which is a constituent protein. As a result, the enzymatic hydrolysis reaction which is a subsequent step is sufficiently carried forward to obtain an amino acid component-containing solution with a high nutritional value. Next the resultant solution is concentrated and dried to obtain, as a powder, the amino acid component useful as a nutrient enhancer for food without especial purification.

For the treatment with ozonized water, the washed and dehydrated fish egg skin is treated in a tank with cold water at room temperature or below for 5 to 30 minutes with stirring while ozone is supplied at a concentration of 0.2 to 10 ppm/L from an ozone generation apparatus. An ozone-treated solution where the fish egg skin is dispersed is warmed up to around 35 to 50° C., optimal for the enzymatic reaction, with stirring in order to make dissolved ozone disappear. After the ozone disappears, the contractile protein (myosin) is degraded with a proteolytic enzyme produced by a microorganism of the Bacillus genus (such as Bacillus subtilis). This degraded solution is directly, or the enzyme in the degraded solution, is warmed up to 80° C. or above, stirred for 15 minutes or longer to inactivate the enzyme. Subsequently using a proteolytic enzyme produced by a microorganism of the Aspergillus genus (such as Aspergillus oryzae), molecular sizes are reduced, and components with bitter taste and amino acid odor derived from other types of the fish spawn proteins are decomposed. The treatments with both enzymes are carried out under the same condition at the treatment temperature of 35 to 55° C. for a treatment time of 2 to 5 hours with stirring wherein each enzyme is used at 0.02 to 0.2% by weight based on the fish egg skin.

For the treated solution after the enzymatic treatment, the enzymes are inactivated, solid materials are then removed by centrifugation using a filter fabric with 800 mesh, and further colloidal impurities are removed by ultra-filtration. The resultant amino acid component-containing filtrate can be utilized as such or as a liquid after condensing to an appropriate concentration depending on intended purposes. For obtaining the amino acid component as a powder, it is desirable to rapidly remove water from the filtrate by normal pressure drying, reduced pressure drying, spray drying, freeze-drying and the like in terms of preventing decomposition of the component as much as possible. From such a view point, the suitable drying methods are reduced pressure drying or spray drying. Also, for the drying temperature, it is desirable to dry at 130° C. or below. When it is over this temperature, active ingredients will be initiated to decompose, thereby leading to deterioration in quality. The preferable drying temperature is from 70 to 130° C.

Thus, in this process, the reduced pressure drying, the spray drying, or other methods lead to the production of powders comprised of amino acid components, wherein peptides and various amino acids are contained. When the amount level of proteolytic enzymes used, especially proteolytic enzymes produced by a microorganism of the Bacillus genus (such as Bacillus subtilis), is low (0.05% or less by weight), peptide-rich amino acid components are obtained. The amino acid component obtained in this process can be utilized per se as a health food supplement, and is useful as a supplement additive to various foods for the purpose of nutrient enhancement. Also, the peptide-rich amino acid component has ACE inhibitory activity.

Additionally, the amino acid component of the present invention may be admixed with any of stabilizers non-toxic to the human body, such as dextrin, vitamins, minerals and the like to enhance its nutritional value. Further, if desired, the amino acid component of the present invention may be utilized in the form of formulations including granules, etc., for example after the amino acid component is admixed with a glanulating agent for foods, known in the art, followed by molding into granules.

Next, the present invention is described in more detail by examples, but the invention is not limited to these examples.

EXAMPLES

Example 1

Spiced Pollack cod roe, Mentaiko, was processed to remove roe grains, the resulting fish egg skin (5 kg) washed three times with cold water (20 L) in a washing bath, and dehydrated by a basket type centrifuging dehydration apparatus. A mixture of the dehydrated fish egg skin (1.5 kg) and cold water (4.5 L) was placed in an enzymatic hydrolysis tank (5 L), and treated with ozonized water at about 10° C. for 10 minutes with stirring while ozone was supplied at the concentration of 0.5 ppm/L from an ozonizer (type 400, K. K. Jarre, J P). The solution was then warmed up to around the enzymatic reaction temperature with stirring in order to make the dissolved ozone disappear. Next, to degrade at about 45° C. the contractile protein (myosin) which was the myogenic fiber protein, protease AROASE AP-10 (produced by Bacillus subtilis, Yakult Pharmaceutical Ind. Co. Ltd., JP) was added at 0.2% by weight based on the weight of the dried fish egg skin, and the mixture was stirred for about 2.5 hours to degrade the contractile protein (myosin).

Further, to the degraded mixture was added protease PANCIDASE NP-2 (produced by Aspergillus oryzae, Yakult Pharmaceutical Ind. Co. Ltd., JP) at 0.2% by weight based on the weight of the fish egg skin, and the mixture was stirred at the same temperature for the same time period to decompose/remove components with bitter taste and amino acid odor derived from fish meat proteins possessed by the fish egg skin and further reduce the molecular sizes.

After enzymatically hydrolyzing with the above two proteolytic enzymes, the treated solution was warmed up to 80° C. to inactivate the residual enzymes and perform sterilization.

The inactivated hydrolysis solution (solution temperature: 60° C.) was supplied with a quantitative pump to a spray drying apparatus at a rate of 200 mL per hour and dried at a dryer inlet hot air temperature of 130° C. and at a dryer outlet hot air temperature of 70° C. to give a powder product with a water content of 7% or less, composed of various amino acids derived from the dried fish egg skin.

REFERENCE EXAMPLE

The enzymatic treatment of Example 1 was repeated using a pretreatment with hot water at 75° C. for 15 minutes in place of the ozone treatment in the example to obtain a powder product with a water content of 7% or less, containing various amino acids derived from the dried fish egg skin.

Analysis results of the amino acid components obtained in the above example and reference example as well as the amino acid component of mackerel extract as described in JP-B-1-14885 are together shown in Table 2 and FIG. 1 as a graph.

TABLE 2

|  | Arg | *Lys | His | *Phe | Tyr | *Leu |
|---|---|---|---|---|---|---|
| Example | 1.34 | 9.75 | 2.34 | 3.57 | 0.73 | 10.19 |
| Reference example | 1.94 | 4.43 | 1.16 | 1.19 | 0.44 | 4.86 |
| Mackerel extract | 3.4 | 4.37 | 2.76 | 1.44 | 1.27 | 3.31 |

|  | *Ile | *Met | *Val | Ala | Gly | Pro |
|---|---|---|---|---|---|---|
| Example | 6.88 | 2.62 | 6.9 | 8.09 | 8.05 | 4.54 |
| Reference example | 3.19 | 1 | 3.18 | 4 | 3.91 | 2.93 |
| Mackerel extract | 1.7 | 1.23 | 2.38 | 3.62 | 4.37 | 2.53 |

|  | Glu | Ser | *Thr | Asp | Cys | Total |
|---|---|---|---|---|---|---|
| Example | 16.53 | 2.71 | 5.12 | 11.23 | 0.43 | 101.02 |
| Reference example | 8.49 | 3.61 | 2.44 | 5.65 | 0 | 53.14 |
| Mackerel extract | 7.46 | 2.24 | 2.14 | 4.43 | 0.27 | 49.23 |

Note: * is an essential amino acid.

As apparent from Table 2 and FIG. 1, it has been observed that the amino acid components obtained from Example 1 are almost comprised of 17 different amino acids, and the content levels of the essential amino acids (7 different amino acids) are remarkably higher than those from the reference example and the mackerel extract. These high amino acid levels indicate that the denaturation or decomposition of the proteins are inhibited by treatment with ozone and that the proteins are nearly completely degraded by the enzymes. In contrast, it is supposed that the low amino acid levels in the reference example and the mackerel extract are due to the denaturation of proteins during the thermal treatment at 70° C. or above.

Example 2

Fish egg skins (40 kg) were washed with water, dried, then sterilized with cold ozonized water (water temperature: 10° C., ozone concentration: 5 ppm). According to the method described in Example 1, the fish meat proteolytic enzyme produced by *Bacillus subtilis* (AROASE AP-10, Yakult Pharmaceutical Ind. Co. Ltd.) was added at 0.03% by weight based on the weight of the dried fish egg skin, and the mixture was stirred for 3 hours to degrade myogenic fiber proteins (myosin, actin). The degraded solution was treated at 85° C. for 15 minutes to inactivate the enzyme.

Further, according to the method described in Example 1, to further reduce the molecular sizes and decompose components with bitter taste, amino acid odor, and the like derived from other types of fish spawn proteins, a protease produced by *Aspergillus oryzae* (NP-2, Yakult Pharmaceutical Ind. Co. Ltd.) was added at 0.03% by weight based on the weight of the dried fish egg skin to the degraded solution in which the enzyme was inactivated, and the mixture was degraded for 3 hours. Subsequently, the same inactivation of the enzyme was repeated to yield a liquid degraded extract (100 L) wherein fish egg skin peptide-containing amino acid components were contained.

This liquid degraded extract was centrifuged by a super centrifuge separator (15,000 rpm, Sharples S NO 6 type, Kokusan Corporation, JP) to remove fine particles, and then passed through an ultra-filtration membrane (NTU-3250, Nitto Denko Co. Ltd., JP) to yield an amino acid component-containing solution wherein the amino acid component included peptides with molecular weights of 6,000 or less. This solution was concentrated to 40 L at 65° C. using a vacuum pressure reduction concentrating apparatus.

The concentrated solution was dried by a spray dryer (Sakamoto Engineering Co. Ltd., DA2SW) to yield a dried material (about 3.6 kg) with a water content of about 4% (average particle size, 50 μm). Analyzed values of the amino acid compositions of said starting solution for filtration and said ultrafiltered liquid are shown in Table 3.

TABLE 3

| Amino Acid | Starting Solution | Ultrafiltration/SD |
|---|---|---|
| Arg | 2.28 | 2.96 |
| *Lys | 2.5 | 3.42 |
| His | 0.86 | 0.7 |
| *Phe | 1.42 | 1.86 |
| Tyr | 1.8 | 2.25 |
| *Leu | 3.39 | 4.4 |
| *Ile | 1.61 | 2.06 |
| *Met | 1.19 | 1.57 |
| *Val | 1.49 | 1.92 |
| Ala | 1.22 | 1.67 |
| Gly | 0.27 | 0.4 |
| Pro | 0.61 | 0.81 |
| Glu | 1.25 | 1.63 |
| Ser | 0.04 | 0.19 |
| *Thr | 0.4 | 0.53 |
| Asp | 0 | 0.09 |
| Cys | 3.96 | 4.74 |

Also, each ACE inhibitory activity in the above starting solution for filtration and the ultrafiltered liquid comprising the peptides and amino acids derived from the above fish egg skin was measured (Lieberman modified method). As a result, the ACE inhibitory activity thereof was observed to be nearly equivalent to that of angiotensin I converting enzyme inhibitory peptides derived from sardines (see: e.g., Non-Patent Document 1).

ACE Inhibitory Activity

Value in the prior art Document 0.754 (mg protein/mL)

Starting solution for filtration 0.87 (mg protein/mL) (M.W. <6000)

Ultrafiltered liquid 1.17 (mg protein/mL)

As described above, enzymatically-degraded fish egg skin solutions each comprising amino acid components or fish egg skin powders obtained from the degraded fish egg skin solution according to the present invention are extremely useful as functional nutrient supplement foods since they are comprised of amino acid components and contain especially lots of essential amino acids. Also ACE inhibitory activity was observed in the amino acid component which contains lots of peptides.

Therefore, the present invention is highly advantageous in terms of environmental pollution because the fish egg skin disposed of as industrial waste is turned to be effectively utilizable.

What is claimed is:

1. A method for producing amino acids and peptides from a fish egg skin, which comprises processing roe grains surrounded by a fish egg skin to remove the roe grains, resulting in a fish egg skin, per se, treating the fish egg skin with ozonized water, resulting in an ozonized water-treated fish egg skin, and treating the ozonized water-treated fish egg skin with a proteolytic enzyme produced by a microorganism of the *Bacillus* genus to degrade contractile proteins which constitute the fish egg skin, to obtain the amino acids and peptides.

2. A method for producing amino acids and peptides from a fish egg skin, which comprises processing roe grains surrounded by a fish egg skin to remove the roe grains, resulting in a fish egg skin, per se, treating the fish egg skin with ozonized water, resulting in an ozonized water-treated fish egg skin, and treating the ozonized water-treated fish egg skin with a proteolytic enzyme produced by a microorganism of the *Bacillus* genus and a proteolytic enzyme produced by a microorganism of the *Aspergillus* genus to degrade contractile proteins which constitute the fish egg skin, to obtain the amino acids and peptides.

* * * * *